(12) United States Patent
Shibayama et al.

(10) Patent No.: US 8,014,960 B2
(45) Date of Patent: Sep. 6, 2011

(54) METHOD OF SUPPORTING A DIAGNOSIS OF A RISK OF CANCER RECURRENCE, AND A DEVICE OF SUPPORTING A DIAGNOSIS OF A RISK OF CANCER RECURRENCE

(75) Inventors: Masaki Shibayama, Kobe (JP); Hideki Ishihara, Miki (JP); Tomoko Matsushima, Kobe (JP); Shigehiro Numada, Kobe (JP)

(73) Assignee: Sysmex Corporation, Hyogo (JP)

( * ) Notice: Subject to any disclaimer, the term of this patent is extended or adjusted under 35 U.S.C. 154(b) by 325 days.

(21) Appl. No.: 12/242,817

(22) Filed: Sep. 30, 2008

(65) Prior Publication Data
US 2009/0246809 A1 Oct. 1, 2009

(30) Foreign Application Priority Data
Mar. 28, 2008 (JP) .................................. 2008-086212

(51) Int. Cl.
*G01N 33/50* (2006.01)
(52) U.S. Cl. ........................... 702/19; 435/7.23; 600/300
(58) Field of Classification Search ........................ None
See application file for complete search history.

(56) References Cited

U.S. PATENT DOCUMENTS
2007/0231837 A1 10/2007 Ishihara et al.

*Primary Examiner* — Karlheinz R Skowronek
(74) *Attorney, Agent, or Firm* — Sughrue Mion, PLLC (57) ABSTRACT

A method of supporting a diagnosis of a risk of cancer recurrence is disclosed. The method provides a new determining value a recurrence risk score (RRS) which is calculated based on expression levels and activity values of two cyclin dependent kinases (CDKs). The risk of cancer recurrence is judged by comparing the RRS with a predetermined threshold level for RRS.

20 Claims, 8 Drawing Sheets

METHOD OF SUPPORTING A DIAGNOSIS OF A RISK OF CANCER RECURRENCE, AND A DEVICE OF SUPPORTING A DIAGNOSIS OF A RISK OF CANCER RECURRENCE

BACKGROUND

Conventionally, serum diagnosis of identifying a tumor marker in blood serum, tissue diagnosis by biopsy, and cytodiagnosis have been known as cancer diagnoses. However, these methods are poor in reliability and give variation in diagnosis resulting from individual assessments or different assessment methods in medical institutes. In recent years, molecular diagnosis based on a gene or protein expressed in living bodies is examined as a standardized cancer diagnostic method with less variation in diagnosis by diagnosticians. As molecular diagnosis based on protein, various methods using a cyclin dependent kinase (also referred to hereinafter as "CDK") have been proposed.

For example, US 2007/231837 describes a method of judging the properties of cells or malignancy of cancers by comparing the CDK specific activity ratio obtained from the activity value/expression level ratio between two CDKs. According to this method, a risk of cancer recurrence can be predicted based on the CDK specific activity ratio between two CDKs from a cancer patient to be examined.

SUMMARY OF THE INVENTION

A first aspect of the invention is a method of supporting a diagnosis of a risk of cancer recurrence, comprising: acquiring an expression level of a first cyclin dependent kinase (CDK), an activity value of the first CDK, an expression level of a second CDK and an activity value of the second CDK from a malignant tumor collected from a cancer patient to be examined; calculating a recurrence risk score based on the following formula (1):

$$\text{recurrence risk score} = F(x) \times G(y) \tag{1}$$

wherein x represents a first CDK specific activity which is able to be calculated by using a ratio of the expression level and the activity value of the first CDK, and y represents a specific activity ratio which is able to be calculated by using a ratio of the first CDK specific activity and a second CDK specific activity wherein the second CDK specific activity is able to be calculated by using a ratio of the expression level and the activity value of the second CDK.

A second aspect of the invention is a method of supporting a diagnosis of a risk of cancer recurrence, comprising: acquiring an expression level of a first cyclin dependent kinase (CDK), an activity value of the first CDK, an expression level of a second CDK and an activity value of the second CDK from a malignant tumor collected from a cancer patient to be examined; calculating a first CDK specific activity which is able to be calculated by using a ratio of the expression level and the activity value of the first CDK, and a second CDK specific activity which is able to be calculated by using a ratio of the expression level and the activity value of the second CDK; and displaying a recurrence risk judgment graph which comprises at least two parameters of a first CDK specific activity and a second CDK specific activity, and is divided into zones different in recurrence risk score calculated based on the following formula (2), wherein the cancer patients to be examined is plotted based on the first CDK specific activity and the second CDK specific activity on the judgment graph, $$\text{recurrence risk score} = F(x) \times G(y) \tag{2}$$

wherein x represents a first CDK specific activity; and y represents a specific activity ratio which is able to be calculated by using a ratio of the first CDK specific activity and the second CDK specific activity.

A third aspect of the invention is a device of supporting a diagnosis of a risk of cancer recurrence, comprising: measurement section for measuring a malignant tumor collected from a cancer patient to be examined to acquire an expression level of a first cyclin dependent kinase (CDK), an activity value of the first CDK, an expression level of a second CDK and an activity value of the second CDK; a controller including a memory under control of a processor, the memory storing instructions enabling the processor to carry out operations which comprise calculating a recurrence risk score based on the following formula (3):

$$\text{recurrence risk score} = F(x) \times G(y) \tag{3}$$

wherein x represents a first CDK specific activity which is able to be calculated by using a ratio of the expression level and the activity value of the first CDK; and y represents a specific activity ratio which is able to be calculated by using a ratio of the first CDK specific activity and the second CDK specific activity wherein the second CDK specific activity is able to be calculated by using a ratio of the expression level and the activity value of the second CDK.

A fourth aspect of the invention is a device of supporting a diagnosis of a risk of cancer recurrence, comprising: measurement section for measuring a malignant tumor collected from a cancer patient to be examined to acquire an expression level of a first cyclin dependent kinase (CDK), an activity value of the first CDK, an expression level of a second CDK and an activity value of the second CDK; a controller system including a display and a memory under control of a processor, the memory storing instructions enabling the processor to carry out operations, comprising: calculating a first CDK specific activity which is able to be calculated by using a ratio of the expression level and the activity value of the first CDK acquired by the measurement section, and a second CDK specific activity which is able to be calculated by using a ratio of the expression level and the activity value of the second CDK acquired by the measurement section; and displaying a recurrence risk judgment graph which comprises at least two parameters of a first CDK specific activity and a second CDK specific activity, and is divided into zones different in recurrence risk score calculated based on the following formula (4), wherein the cancer patients to be examined is plotted based on the first CDK specific activity and the second CDK specific activity on the judgment graph, $$\text{recurrence risk score} = F(x) \times G(y) \tag{4}$$

wherein x represents a first CDK specific activity; and y represents a specific activity ratio which is able to be calculated by using a ratio of the first CDK specific activity and the second CDK specific activity.

DETAILED DESCRIPTION OF THE PREFERRED EMBODIMENTS

[1] Method of Judging a Risk of Cancer Recurrence

The judgment method according to a first aspect of the invention is a method of determining a risk of cancer recurrence, comprising acquiring expression levels and activity values of a first cyclin dependent kinase (CDK) and a second CDK from a malignant tumor collected from a cancer patient to be examined, determining a recurrence risk score based on the obtained expression levels and activity values of the first CDK and the second CDK, and judging a risk of cancer recurrence based on the obtained recurrence risk score.

The "recurrence" in this specification includes the case where after an organ is partially eliminated for extirpating a malignant tumor, the same malignant tumor reappears in the remaining organ, and the case where a cancerous cell is separated from a primary tumor and carried into a distant tissue (distant organ) and proliferates autonomously therein.

The "risk of recurrence" in this specification means the risk of cancer recurrence in the body of a cancer patient from whom a malignant tumor has been extirpated, and the risk of death of the patient by cancer recurrence. Unless otherwise noted, the "risk of recurrence" includes both the risks.

(1) Step of Acquiring the Expression Levels and Activity Values of the First CDK and the Second CDK from a Malignant Tumor Collected from a Cancer Patient to be Examined Malignant tumors collected from cancer patients to be examined may be for example cells constituting supporting tissues in biological tissues of the patients, such as fibrous connective tissue, cartilage tissue, bone tissue, blood and lymph; epithelium tissue; muscle tissue; and nervous tissue. Particularly, the cell used in the judgment method in this embodiment is preferably a cell required to obtain pathological information, such as a tumor cell derived from the tissue which breaks a balance in an individual and dysfunctions in growth regulation. Preferable examples of the tumor cell include a cell derived from a tumor generated in organs such as breast, lung, liver, stomach, colon, pancreas, skin, uterus, testis, ovary, thyroid gland, parathyroid gland, lymphatic system, and bone marrow.

The cyclin dependent kinase (CDK) is a generic term for various enzymes activated by binding to cyclin, and does not have an activity by itself, but becomes an activated form by binding to cyclin. The CDK acts in a specific phase of a cell cycle depending on its kind. The CDK includes CDK1, CDK2, CDK4, CDK6, cyclin A dependent kinase, cyclin B dependent kinase, and cyclin D dependent kinase.

From plural kinds of CDKs listed herein, a first CDK and a second CDK are determined, and the expression levels and activity values of the first CDK and the second CDK of a malignant tumor collected from a cancer patient to be examined are measured.

The CDK activity value refers to kinase activity level (U) which is calculated from an amount of a substrate to be phosphorylated upon the binding of CDK to a specific cyclin. The substrate to be phosphorylated with the CDK includes histone H1 for activated CDK1 and activated CDK2 as well as Rb (retinoblastoma protein) for activated CDK4 and activated CDK6.

The CDK activity value can be measured by any conventional method of measuring CDK activity. For example, there is a method which comprises preparing a sample containing activated CDK from a cell lysate as a measurement sample, then using the sample and $^{32}$P-labeled ATP ($\gamma$-[$^{32}$P]-ATP) so that a substrate protein is allowed to incorporate $^{32}$P, measuring the labeling amount of the phosphorylated substrate labeled with $^{32}$P, and quantitatively determining the activity values based on a standard curve previously prepared using standard samples. As a method using no labeling by radioactive substance, there is a method which comprises preparing a sample containing activated CDK of interest from a cell lysate of a subject, reacting the substrate with adenosine 5'-O-(3-thiotriphosphate) (ATP-$\gamma$S) to introduce monothiophosphate group into serine or threonine residue in the substrate protein, labeling the substrate protein by binding a fluorescent substance or a labeled enzyme to a sulfur atom in the introduced monothiophosphate group, measuring the amount of the labeled thiophosphorylated substrate (or the amount of the fluorescent substance in the case where the fluorescent substance is used), and quantitatively determining the phosphoric acid amount based on a standard curve previously prepared using standard samples.

US 2002-164673 is hereby incorporated by reference in its entirely as though fully and completely set forth herein.

Samples subjected to activity measurement are prepared by specifically collecting CDK of interest from lysates of tissues containing malignant tumors to be measured. The sample may be prepared by using an anti-CDK antibody specific to CDK of interest. In the case where the activity of a specific cyclin dependent kinase (for example, cyclin A dependent kinase, cyclin B dependent kinase or cyclin E dependent kinase) is measured, the sample may be prepared using an anti-cyclin antibody. In both cases, CDK other than activated CDK is contained in the sample. For example, the cyclin-CDK complex to which a CDK inhibitor is bound may also be contained in the sample. When the anti-CDK antibody is used, CDK itself, a CDK-cyclin complex, a CDK-CDK inhibitor complex, and/or complexes of CDK and other compounds are contained. Accordingly, CDK activity value is measured in terms of the unit (U) of the phosphorylated substrate under the condition where various CDKs such as activated CDK, inactivated CDK, and various competitive reactive substances co-exist.

The CDK expression level is an amount of target CDK (unit corresponding to the number of molecules), which is contained in a cell lysate from tissues containing malignant tumors to be measured, and can be measured by a known method of measuring the amount of a target protein in a protein mixture. For example, an enzyme-linked immunosorbent assay (ELISA) or a Western blot process may be used. The target protein (CDK) can be captured by using an antibody specific to the target protein. For instance, an anti-CDK1-antibody can be used to capture all CDK1s present in cells (for example, CDK itself, a CDK-cyclin complex, a CDK-CDK inhibitor complex, and/or complexes of CDK and other compounds).

US 2004/0214180 is hereby incorporated by reference in its entirely as though fully and completely set forth herein.

(2) Step of Calculating a Recurrence Risk Score

Recurrence risk score (RRS) is determined on the basis of the activity value/expression level ratio between the two CDKs obtained in the above step. The recurrence risk score (RRS) is determined according to the following formulas (5) to (7):

$$RRS = F(x) \times G(y) \quad (5)$$

$$F(x) = a/(1 + \text{Exp}(-(x-b) \times c)) \quad (6)$$

$$G(y) = d/(1 + \text{Exp}(-(y-e) \times f)) \quad (7)$$

wherein a to f represent a constant.

In the formulas, x represents the first CDK specific activity, and y represents the specific activity ratio. The CDK specific activity is calculated by a ratio of the CDK activity value and CDK expression level, and the specific activity ratio is calculated by a ratio of the second CDK specific activity and the first CDK specific activity. The formulas (5) to (7), the specific activity and the specific activity ratio will be described later in more detail.

(3) Step of Judging a Risk of Recurrence Based on a Recurrence Risk Score

The recurrence risk score RRS obtained as described above is compared with a predetermined threshold value to judge a risk of cancer recurrence. For example, when the recurrence risk score RRS of a cancer patient to be examined is compared with a threshold value, and when the recurrence risk score (RRS) of the cancer patient to be examined is higher than the threshold value, the risk of cancer recurrence in the cancer patient to be examined can be judged to be high, while when the recurrence risk score (RRS) of the cancer patient to be examined is lower than the threshold value, the risk of cancer recurrence in the cancer patient to be examined can be judged to below, and therefore the risk of cancer recurrence can be judged.

The threshold value can be appropriately established depending on the object (prognosis, decision on therapeutic strategy or the like) of the judgment of a risk of cancer recurrence.

The threshold value can be established by various methods. For example, tumor cells collected from a plurality of cancer patients having known malignancy grading judged by a medical pathologist are used to calculate the recurrence risk score RRS based on the above formula, and the recurrence risk score RRS by which the patients can be classified into 2 groups wherein one group is recognized to have cancer recurrence and the other group is not recognized to have cancer recurrence can be established as the threshold value. The recurrence risk can be judged to be "high" or "low" by judging the possibility of cancer recurrence by the threshold value established in this manner.

For example, the recurrence risk score RRS by which cancer patients having malignancy grading judged by a medical pathologist can be classified into 2 groups such that 80% of the cancer patients classified by the recurrence risk score RRS are cancer patients recognized to have cancer recurrence can be a threshold value. By establishing the threshold value in this way, the recurrence risk can be judged to be high when the cancer recurrence rate is 80% or higher. Alternatively, a plurality of threshold values may be established for different recurrence rates so that a risk of cancer recurrence can be evaluated and judged in stages.

The reason that the recurrence risk score RRS can be calculated from the formulas (5) to (7) is herein described.

First, the meanings of the CDK specific activity and specific activity ratio are described.

The CDK specific activity is expressed as the CDK activity value/CDK expression level ratio and thus refers to the ratio of the CDK activity value to the expression level. The CDK specific activity is a parameter that reflects the CDK enzyme activity per unit CDK protein mass contained in a sample, corresponds to the ratio of active CDK to CDK occurring in cells, and shows the CDK activity level based on the proliferating state of malignant tumor cells to be judged.

The specific activity ratio is expressed as the second CDK specific activity/first CDK specific activity ratio and thus refers to the ratio of the second CDK specific activity to the first CDK specific activity. The CDK specific activity ratio is the ratio between the activity levels of two CDKs each exhibiting an activity in a specific cell cycle, and is a parameter that reflects which of the CDK activities in cancer patient's cells is predominant (which degree of cells are in which stage of cell cycle).

Generally, since a cancer cell is out of normally controlled growth and proliferates rapidly, when the ratio of cells staying in the period between S phase (DNA replicative period) and G2 phase (period of from termination of DNA synthesis to initiation of mitotic division) is high, the cells can be estimated to become cancerous. The aneuploidity is considered to be caused by passing through an abnormal M phase (cell division stage), or proceeding to G1 phase and then S phase without undergoing M phase. Therefore, the sample in which the ratio of cells in M phase is low may be estimated to become cancerous.

Accordingly, it is preferable that for example, CDK1 showing an activity during shifting from G2 phase to M phase in cell cycle be used as the first CDK, and CDK2 showing an activity during shifting from G1 phase to S stage in cell cycle be used as the second CDK. By determining the CDK specific activity ratio based on these two CDKs, a numerical value reflecting how much the cells in the S or G2 phase occur relative to the cells in the M phase can be obtained. This numerical value can be used as a parameter reflecting the proliferating ability of the cells.

Then, the formulas (5) to (7) for calculating the recurrence risk score (RRS) are described.

As illustrated above, parameters correlated with the proliferating ability of cells (risk of cancer recurrence) can be obtained by obtaining the CDK specific activity ratio based on the first CDK specific activity and the second CDK specific activity.

However, there can be cases where the CDK specific activity ratio is not correlated with the proliferating ability of cells (risk of cancer recurrence). For example, when the CDK specific activity ratio is determined by using CDK1 as the first CDK and CDK2 as the second CDK as illustrated above, the CDK specific activity ratio is low when the CDK1 specific activity is abnormally high. But, from another viewpoint, this low ratio can be also considered attributable to abnormal activation of CDK1 by high expression of cyclin that has formed a complex with CDK1.

It is considered that even if the amount of CDK activated in a certain cell cycle is low, cells can proliferate by compensatory function of another specific CDK, so abnormal activation of specific CDK can be also considered attributable to abnormal cellular kinetics.

Accordingly, the inventors have estimated that a risk of cancer recurrence can be determined by two risk factors: (1) first CDK specific activity and (2) second CDK/first CDK specific activity ratio, and they have found a method of evaluating a risk of cancer recurrence based on these risk factors.

First, the probabilities of cancer recurrence based on the risk factors (1) and (2) respectively are expressed as risk score RS (1) and risk score RS (2) by using numerically evaluated scales. The probabilities of cancer recurrence resulting from the risk factors (1) and (2) are expressed as recurrence risk score RRS by using a numerically evaluated scale. As a consequence, the probability of cancer recurrence, that is, recurrence risk, is given by a product obtained by multiplying the probability of cancer recurrence resulting from the risk factor (1) by the probability of cancer recurrence from the risk factor (2), and therefore, the recurrence risk score (RRS) is given by a value proportional to the product of the risk score RS (1) and the risk score RS (2). Accordingly, the following formula (8) can hold:

$$RRS = RS(1) \times RS(2) \quad (8)$$

The risk score RS (1) and risk score RS (2) can be determined in the following manner.

Figure 1A:
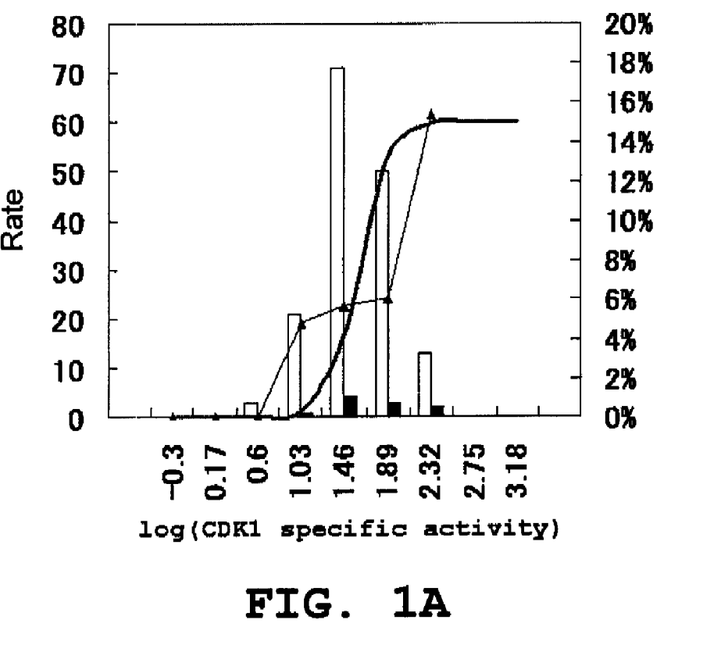
FIG. 1A is a histogram showing the relationship between the CDK1 specific activity obtained from a plurality of cancer patients to be examined and the cancer recurrence rate.
Figure 1B:
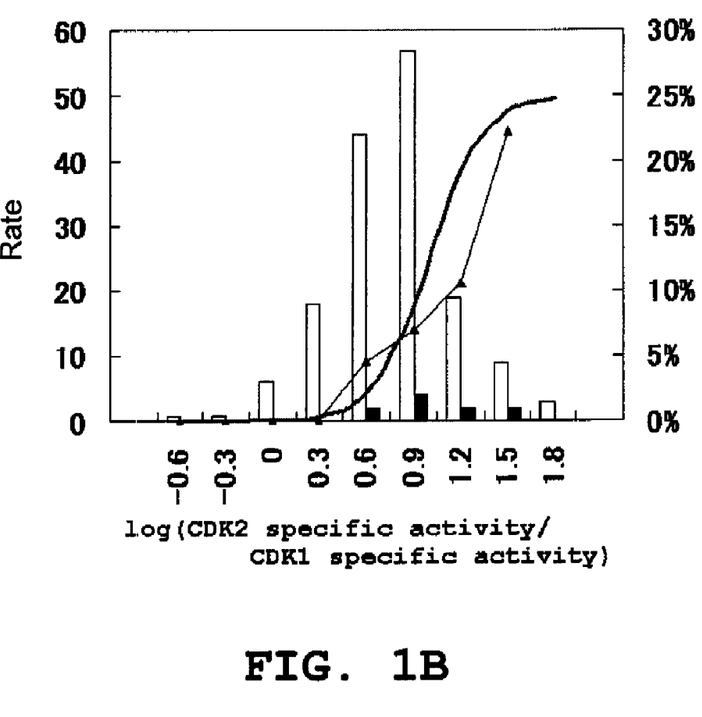
FIG. 1B is a histogram showing the relationship of the specific activity ratio between CDK1 and CDK2 from a plurality of cancer patients to be examined and the cancer recurrence rate.

FIG. 1A is a histogram showing the relationship between the CDK1 specific activity obtained from a plurality of cancer patients to be examined and their cancer recurrence rate, and FIG. 1B is a histogram showing the relationship between the CDK2/CDK1 specific activity ratio obtained from a plurality of cancer patients to be examined and their cancer recurrence rate. In this graph, a plurality of cancer patients to be examined are classified according to the CDK1 specific activity or the CDK2/CDK1 specific activity ratio obtained from the cancer patients, and the total number of patients contained in each class is shown in white bar, and the number of patients having recurrence contained in each class is shown in shaded bar. Further, the probability of cancer recurrence (number of patients having recurrence/total number of patients) in each case is shown in line graph.

As can be seen from the graph, the probability of cancer recurrence is flatly increased according to the CDK1 specific activity or the CDK2/CDK1 specific activity ratio. Accordingly, the possibility of cancer recurrence in each class can be approximated, thereby giving risk score RS (1) having the CDK1 specific activity as risk factor and risk score RS (2) having the CDK2/CDK1 specific activity ratio as risk factor. Accordingly, the probability of cancer recurrence in each class is approximated by logistic function wherein the CDK1 specific activity is expressed as x, and the CDK2/CDK1 specific activity ratio is expressed as y, and the risk score RS (1) and risk score RS (2) are obtained in the following formulas (9) and (10):

$$RS(1); F(x) = a/(1 + \mathrm{Exp}(-(x-b) \times c)) \quad (9)$$

$$RS(2); G(y) = d/(1 + \mathrm{Exp}(-(y-e) \times f)) \quad (10)$$

wherein a to f represent a constant.

From the foregoing, the recurrence risk score RRS is expressed by the following formula (11) to derive the formula (5).

$$RRS = F(x) \times G(y) \quad (5)$$

In the embodiment described above, a method of judging a risk of cancer recurrence by calculating the recurrence risk score RRS and then comparing it with a threshold value has been described, but without limitation thereto, a method wherein a risk of cancer recurrence is judged with another judgment criterion may be used.

For example, the method of judging a risk of cancer recurrence can be constituted wherein the first CDK specific activity is calculated separately from the recurrence risk score RRS; the recurrence risk score RRS is used as a first judgment criterion and the first CDK specific activity is used as a second judgment criterion; and on the basis of the two judgment criteria, the risk of recurrence is judged.

Specifically, the expression levels and activity values of the first CDK and second CDK from a cancer patient to be examined are acquired, and the recurrence risk score RRS and the first CDK specific activity are calculated.

Then, the recurrence risk score RRS and the first CDK specific activity thus obtained are compared the corresponding threshold values to judge the risk of recurrence.

More specifically, a first threshold value is set as the threshold value for the recurrence risk score RRS, and a second threshold value is set as the threshold value for the first CDK activity. When either the recurrence risk score RRS or the first CDK specific activity obtained from the cancer patient to be examined is higher than the corresponding threshold value, the risk of cancer recurrence is judged to be high. When both the recurrence risk score RRS and the first CDK specific activity are lower than the corresponding threshold values, the risk of cancer recurrence is judged to be low.

Each of the first and second threshold values may contain two or more threshold values. For example, first threshold values a and b are previously set as the first threshold value, and second threshold values a and b are set as the second threshold value. Then, when the recurrence risk score RRS is the first threshold value a or higher, or when the first CDK specific activity is the second threshold value a or higher, the recurrence risk is judged to be high; when the recurrence risk score RRS is lower than the threshold value b and the first CDK specific activity is lower than the second threshold value b, the risk of cancer recurrence is judged to be low; and when the recurrence risk score RRS is lower than the first threshold value a and the second threshold value b or higher and simultaneously the first CDK specific activity is lower than the second threshold value and the second threshold value b or higher, the recurrence risk is judged to be intermediate.

In this manner, the risk of cancer recurrence can be judged more accurately by judging a risk of cancer recurrence with the recurrence risk score RRS and another judgment criterion.

In this embodiment, there is provided a method for supporting diagnosis of a risk of cancer recurrence by displaying a judgment graph for judging a risk of recurrence.

Figure 2A:
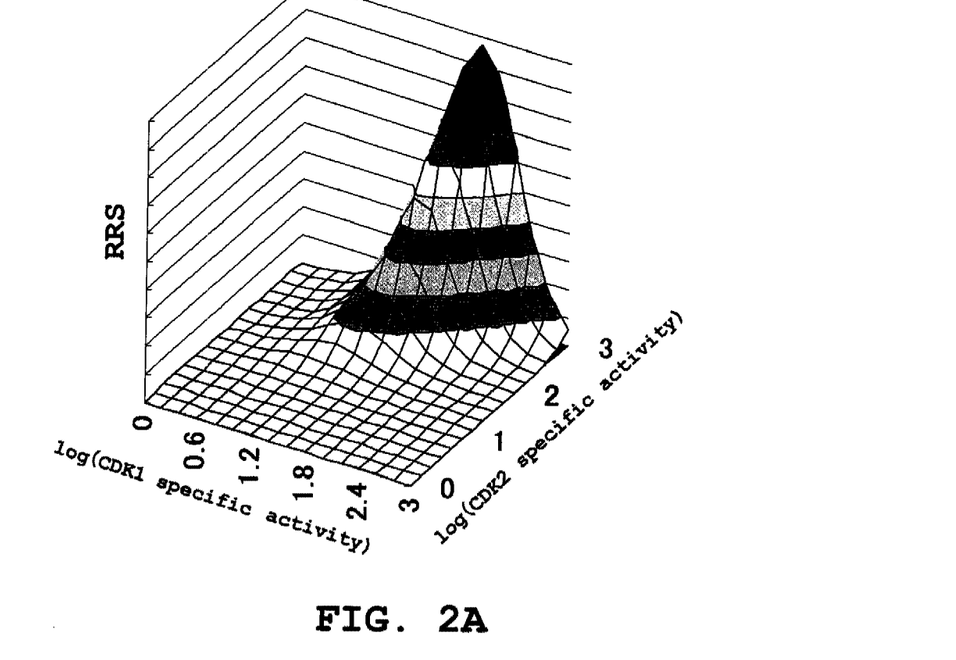
FIG. 2A is a three-dimensional graph showing a logarithm of CDK1 specific activity (x-axis), a logarithm of CDK2 specific activity (y-axis) and recurrence risk score RRS (z-axis) as parameters.
Figure 2B:
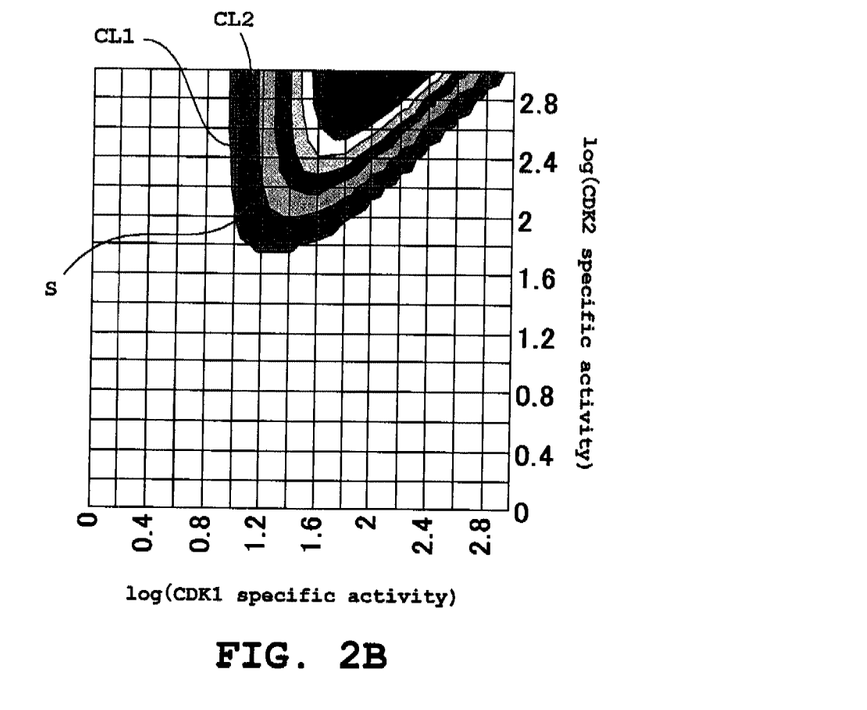
FIG. 2B is a two-dimensional, projected plan of the recurrence risk score RRS (z-axis) in FIG. 2A.

FIG. 2 is a view for schematically explaining the recurrence risk score RRS described above. FIG. 2A is a three-dimensional graph with a logarithm of CDK1 specific activity (x-axis), a logarithm of CDK2 specific activity (y-axis), and recurrence risk score (RRS) (z-axis) as parameters. FIG. 2B is a two-dimensional, projected plan of the recurrence risk score RRS (z-axis) in FIG. 2A.

When the recurrence risk score RRS is projected on a second-dimensional graph as shown in FIG. 2B, a plurality of contour curves each showing the same risk score RRS are drawn.

For example, every point on curve CL1 is a point indicating the CDK1 and CDK2 specific activities giving the same recurrence risk score RRS. This also applies to every point on curve CL2.

Then, the zone surrounded by a curve is always a zone wherein the recurrence risk score is higher than the point on the curve (see FIG. 2A). For example, when the curve CL1 is a curve drawn by connecting points at which the recurrence risk score RRS=M, the zone surrounded by the curve CL1 is a zone in which the recurrence risk score RRS is equal to or higher than M. When the curve CL1 is a curve drawn by connecting points at which the recurrence risk score RRS is a predetermined value M, and simultaneously the curve CL2 is a curve drawn by connecting points at which the recurrence risk score RRS is a predetermined value N, the zone S surrounded by the curves CL1 and CL2 is a zone in which the relationship: M≦(recurrence score)<N is satisfied.

As described above, a two-dimensional graph composed of the first CDK specific activity (x-axis) and the second CDK specific activity (y-axis) can be divided into zones that are made different in recurrence risk score by curves (cutoff lines) each being drawn by connecting point at which the recurrence risk score RRS is the same.

The judgment graph for judging a risk of cancer recurrence can be prepared in the following manner.

First, a threshold value is established for the recurrence risk score RRS. The threshold value for the recurrence risk score RRS may be a value serving as a criterion that can judge a risk of cancer recurrence. For example, the threshold value is a value by which patients can be classified into those having a high recurrence risk and those having a low recurrence risk, depending on whether their RRS is higher or lower than the threshold value.

Then, a cutoff line is formed by connecting points at which the recurrence risk score RRS is the threshold value on the two-dimensional graph comprising two parameters that are the first CDK specific activity and the second CDK specific activity. Thereby, dividing the two-dimensional graph into two zones wherein in one zone, the recurrence risk score RRS is higher than the threshold value, and in the other zone, the recurrence risk score RRS is lower than the threshold value is conducted. This cutoff line has been prepared on the basis of the value serving as a criterion that can judge a risk of cancer recurrence, so the two-dimensional graph can be divided into zones different in recurrence risk. The recurrence risk judgment graph is prepared in this manner.

The first CDK specific activity and the second CDK specific activity calculated from the expression levels and activity values of the first CDK and second CDK obtained from a malignant tumor of a tumor patient to be examined are plotted on the recurrence risk judgment graph. The recurrence risk judgment graph has been divided into the zones that are made different in recurrence risk by a plurality of cutoff lines indicating threshold values, so that when the first CDK specific activity and second CDK specific activity of the cancer patient to be examined are plotted on the recurrence risk judgment graph, whether the risk of cancer recurrence in the patient is high or low can be judged at a glance. When the recurrence risk judgment graph is displayed, the medical doctor can judge the risk of cancer recurrence in a patient by glancing at the judgment graph, and can provide information useful in diagnosis of the risk of recurrence in the patient.

Figure 3:
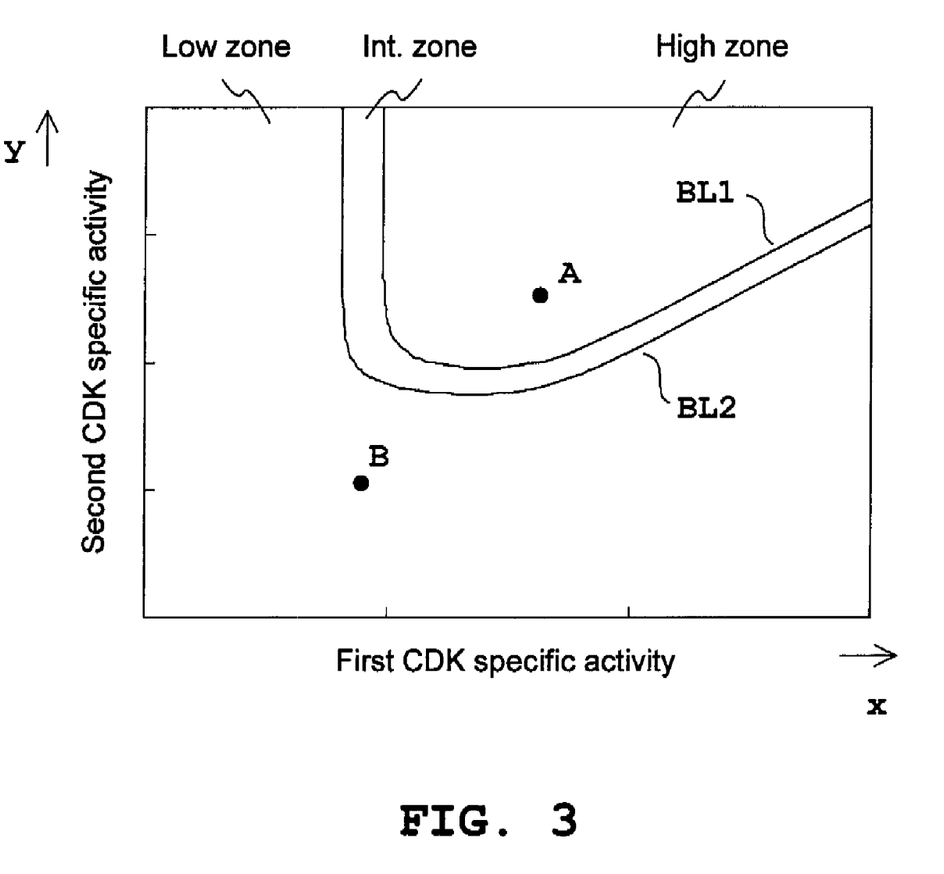
FIG. 3 is an example of a recurrence risk judgment graph used in a supporting method in this embodiment.

FIG. 3 is an example of the recurrence risk judgment graph used in a method of supporting diagnosis of a risk of cancer recurrence according to this embodiment. This recurrence risk judgment graph shows the first CDK specific activity on the x-axis and the second CDK specific activity on the y-axis, wherein the distribution zone is divided by cutoff lines BL1 and BL2 into 3 zones, that is, a zone of high recurrence risk (High zone), a zone of low recurrence risk (Low zone), and a zone of intermediate recurrence risk (Int. zone).

Now, it is assumed that on the basis of the first CDK specific activity and the second CDK specific activity obtained from a certain cancer patient A, point A is plotted on the recurrence risk judgment graph. As shown in FIG. 3, the point A is placed on High zone surrounded by the cutoff line BL1, so the cancer patient A can be judged to have a high risk of cancer recurrence.

Similarly, it is assumed that on the basis of the first CDK specific activity and the second CDK specific activity obtained from a certain cancer patient B, point B is plotted on the recurrence risk judgment graph. As shown in FIG. 3, the point B is placed on Low zone surrounded by the cutoff line BL2, so the cancer patient B can be judged to have a low risk of cancer recurrence.

The recurrence risk judgment graph may be a judgment graph for judging a risk of cancer recurrence on the basis of the recurrence risk score RRS and another judgment criterion. For example, the recurrence risk judgment graph may be a judgment graph for judging a risk of cancer recurrence by two judgment criteria composed of the recurrence risk score RRS as a first judgment criterion and the first CDK specific activity as a second judgment criterion. This judgment graph can be prepared in the following manner.

As threshold values effective in judgment of a risk of cancer recurrence, the first threshold values a and b for the recurrence risk score RRS and the second threshold values a and b for the first CDK specific activity are first established. Then, a curve drawn by joining points indicating the first threshold value a for the recurrence risk score RRS is joined to a line drawn by joining points indicating the second threshold value a for the first CDK specific activity, on the two-dimensional graph composed of two parameters, i.e. the first CDK specific activity and the second CDK specific activity, thereby forming a first cutoff line. Similarly, a curve drawn by joining points indicating the first threshold value b for the recurrence risk score RRS is joined to a line drawn by joining points indicating the second threshold value b for the first CDK specific activity, thereby forming a second cutoff line. A recurrence risk judgment graph divided into zones that are made different in cancer recurrence risk according to the recurrence risk score RRS and the first CDK specific activity can be thereby prepared. One example is shown in FIG. 4.

Figure 4:
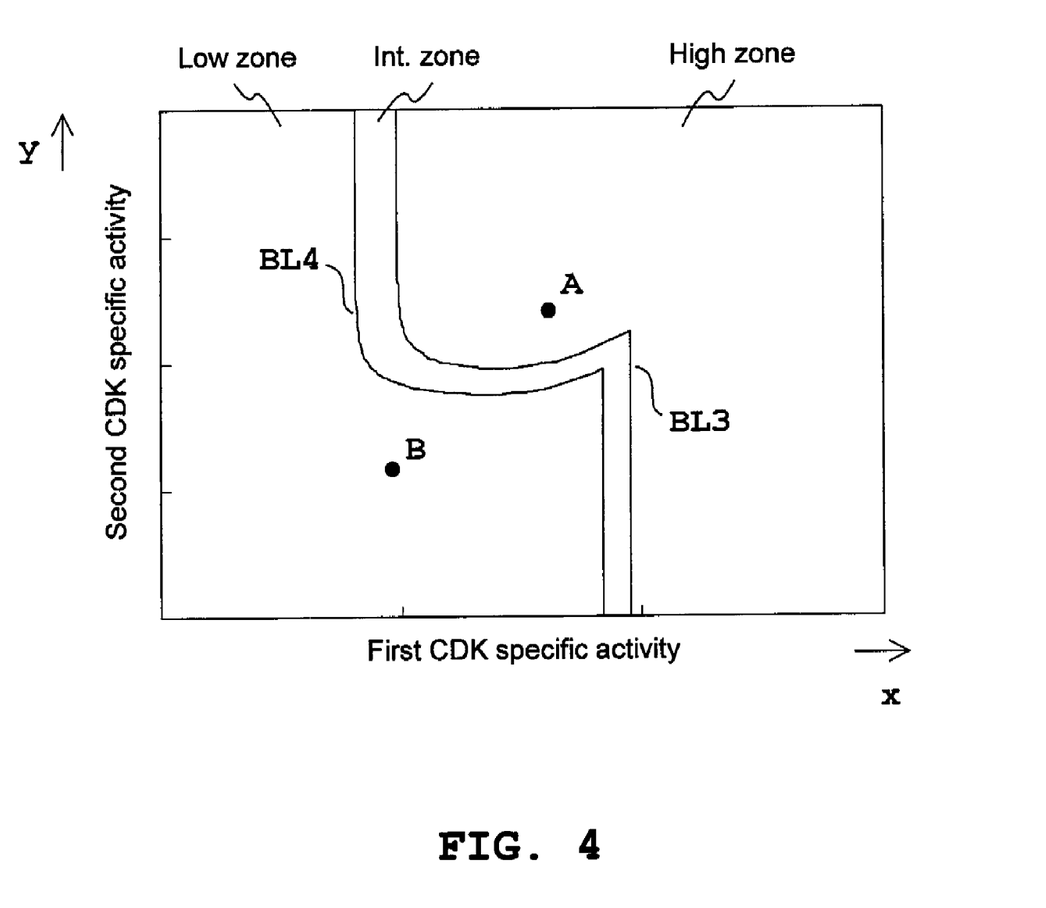
FIG. 4 is another example of a recurrence risk judgment graph used in a supporting method in this embodiment.

FIG. 4 is an example of the recurrence risk judgment graph used in a method of supporting diagnosis of a risk of cancer recurrence according to this embodiment. This recurrence risk judgment graph shows the first CDK specific activity on the x-axis and the second CDK specific activity on the y-axis, wherein the distribution zone is divided by cutoff lines BL3 and BL4 into 3 zones, that is, a zone of high recurrence risk (High zone), a zone of low recurrence risk (Low zone), and a zone of intermediate recurrence risk (Int. zone). In FIG. 4, the cutoff line BL3 is a line in which a curve drawn by joining points indicating the first threshold value a for the recurrence risk score RRS is joined to a line drawn by joining points indicating the second threshold value a for the first CDK specific activity. The cutoff line BL4 is a line in which a curve drawn by joining points indicating the first threshold value b for the recurrence risk score RRS is joined to a line drawn by joining points indicating the second threshold value b for the first CDK specific activity.

That is, High zone that is a zone surrounded by the cutoff line BL3 is a zone wherein the recurrence risk score RRS is the first threshold value a or higher, or the first CDK specific activity is the second threshold value a or higher. On the other hand, Low zone that is a zone surrounded by the cutoff line BL4 is a zone wherein the recurrence risk score RRS is lower than the first threshold value b, and the first CDK specific activity is lower than the second threshold value b.

By displaying the recurrence risk judgment graph based on the two judgment criteria, i.e. the recurrence risk score RRS and the first CDK specific activity, information for supporting more reliable diagnosis can be provided.

[2] Judgment Device

Then, the device for judging a risk of cancer recurrence in this embodiment is described.

Figure 5:
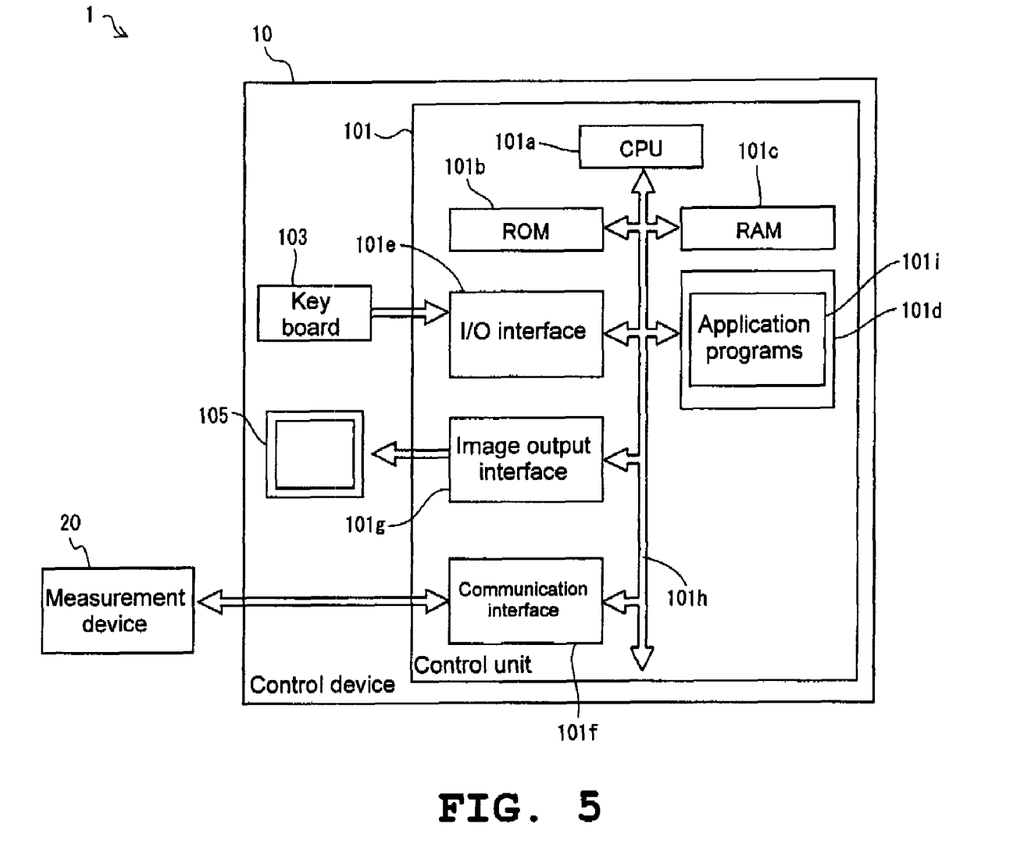
FIG. 5 is a block diagram showing a framework of the judgment device in this embodiment.

FIG. 5 is a block diagram showing a framework of the judgment device in this embodiment. The judgment device 1 in this embodiment is a device for judging a risk of cancer recurrence in a cancer patient to be examined, on the basis of data obtained from the cancer patient to be examined and is constituted by a control device 10 and a measurement device 20 as shown in FIG. 5. The control device 10 is a device that analyzes measurement data output by the measurement device 20 to judge a risk of cancer recurrence and outputs the judgment result, and the measurement device 20 is a device that measures a malignant tumor collected from a cancer patient to be examined and outputs the measurement data to the control device 10.

The control device 10 comprises a personal computer (PC) and includes a control unit 101, a keyboard 103 and a display unit 105. The control unit 101 includes CPU 101a, ROM 101b, RAM 101c, a hard disk 101d, an image output interface 101e, a communication interface 101f, an image output interface 101g, and bus 101h, and the respective parts are connected to one another via bus 101h to mutually transmit and receive data.

The CPU 101a can execute computer programs stored in the ROM 101b and computer programs loaded on the RAM 101c. The ROM 101b stores computer programs executed by the CPU 101a and data for executing these computer programs. The RAM 101c is used to read computer programs stored in the ROM 101b and hard disk 101d. The RAM 101c is also used as a work area for the CPU 101a when executing these computer programs.

Installed in the hard disk 101d are various computer programs to be executed by the CPU 101a such as an operating system (OS) and application programs, and various data used for executing these computer programs.

The application program 101i installed in the hard disk 101d includes an application program for realizing the method of judging a risk of cancer recurrence.

An I/O interface 101e has a keyboard 103 and a mouse (not shown) connected thereto. A communication interface 101f has the measurement device 20 connected thereto, and via the communication interface 101f, data can be transmitted and received between the control unit 101 and the measurement device 2.

The image output interface 101g is connected to the display unit 105 and outputs an image signal corresponding to image data given by CPU 101a to the display unit 105. The display unit 105 displays an (on-screen) image according to the input image signal.

The measurement device 20 connected via the communication interface 101f to the control device 10 is a device for measuring the expression level and activity value of CDK from a biological tissue. A conventionally known device for judging tissue properties can be used as a measurement device for measuring the CDK expression level and CDK activity value from a biological tissue.

US 2007/0077658 is hereby incorporated by reference in its entirely as though fully and completely set forth herein.

In this embodiment, the judgment device 1 is constituted so as to receive measurement data obtained by the measurement device 20 and to judge a risk of cancer recurrence, but may, without limitation to such constitution, be constituted such that measurement data on the previously measured CDK expression level and CDK activity value are inputted via the keyboard 103.

Figure 6:
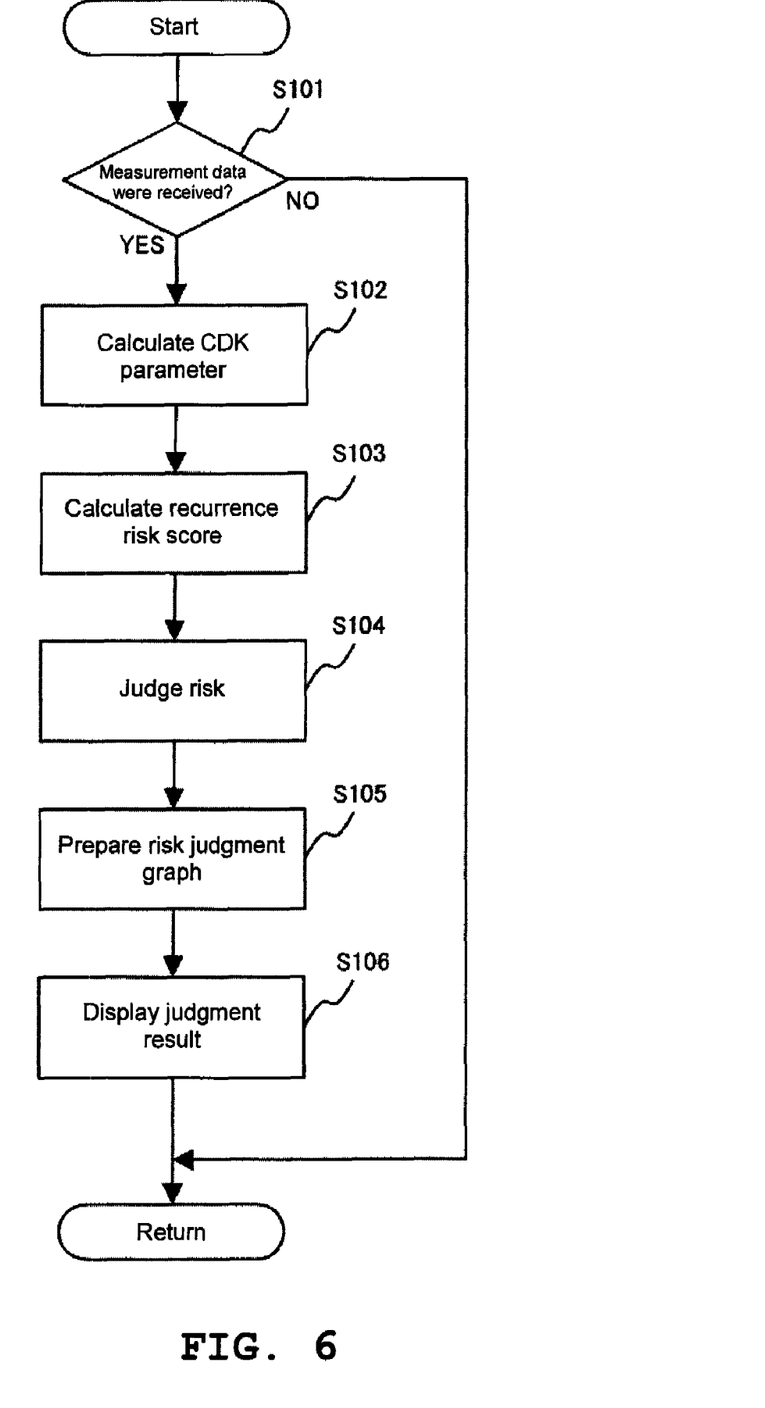
FIG. 6 is a flowchart showing a processing for judging a risk of cancer recurrence by the judgment device in this embodiment.

FIG. 6 is a flowchart showing processing for judging a risk of cancer recurrence by the judgment device 1 in this embodiment.

To realize the processing according to this flowchart, the application program 101i installed in the hard disk 101d is read by RAM 101c, and the CPU 101a executes the application program 101i read by the RAM 101c.

First in step S101, CPU 101a executes processing for judging whether measurement data are received or not from the measurement device 20. When CPU 101a judges that measurement data from the measurement device 20 are not received (NO in step S101), the processing is returned.

As used herein, the measurement data refer to the expression levels and activity values of at least two CDKs obtained by measuring a biological tissue with the measurement device 20.

When CPU 101a judges that measurement data from the measurement device 20 are received (YES in step S101), the processing advances to step S102 in which processing for calculating CDK parameters is executed on the basis of the measurement data containing the expression levels and activity values of at least two CDKs received from the measurement device 20.

The CDK parameters calculated in step S102 are the first CDK specific activity, the second CDK specific activity and the CDK specific activity ratio.

Then, the processing advances to step S103, and CPU 101a executes processing for calculating recurrence risk score RRS.

The formula for calculating recurrence risk score RRS based on the expression levels and activity values of the first CDK and the second CDK is integrated in the application program 101i, and the CPU 101a executes the application program 101i, thereby calculating the recurrence risk score RRS.

Then, the processing advances to step S104, and the CPU 101a executes processing for judging recurrence risk. This processing is carried out by comparing the CDK parameters and recurrence risk score RRS calculated in steps S102 and S103 with the first and second threshold values set in the application program 101i. The first threshold value includes the first threshold value a and the first threshold value b, and the second threshold value includes the second threshold value a and the second threshold value b.

By CPU 101a, the recurrence risk is judged to be "high" when the recurrence risk score RRS is the first threshold value a or higher or when the first CDK specific activity is the second threshold value a or higher; the recurrence risk is judged to be "low" when the recurrence risk score RRS is lower than the first threshold value band simultaneously the first CDK specific activity is lower than the second threshold value b; and when the recurrence risk is judged to be "intermediate" when the recurrence risk score RRS is lower than the first threshold value a and is the first threshold value b or higher and when the first CDK specific activity is lower than the second threshold value a and is the second threshold value b or higher.

Then, the processing advances to step S106, and CPU 101a executes processing for preparing a recurrence risk judgment graph.

The recurrence risk judgment graph is a two-dimensional graph composed of two parameters, i.e. the first CDK specific activity and the second CDK specific activity, wherein the distribution zone is divided into zones different in recurrence risk. Each zone in this two-dimensional graph is divided by a cutoff line wherein a curve drawn by connecting points at which the recurrence risk score RRS is the first threshold value a is joined to a line drawn by connecting points at which the recurrence risk score RRS is the second threshold value b, and by a cutoff line wherein a curve drawn by connecting points at which the recurrence risk score RRS is the first threshold value b is joined to a line drawn by connecting points at which the first CDK specific activity is the second threshold value b. Samples whose recurrence risks were judged are plotted on this two-dimensional distribution graph.

The processing then advances to step S106, and CPU 101a executes processing in which the recurrence risk judgment result obtained in step S104 and the recurrence risk judgment graph prepared in step S105 are displayed on the display unit S105.

Figure 7:
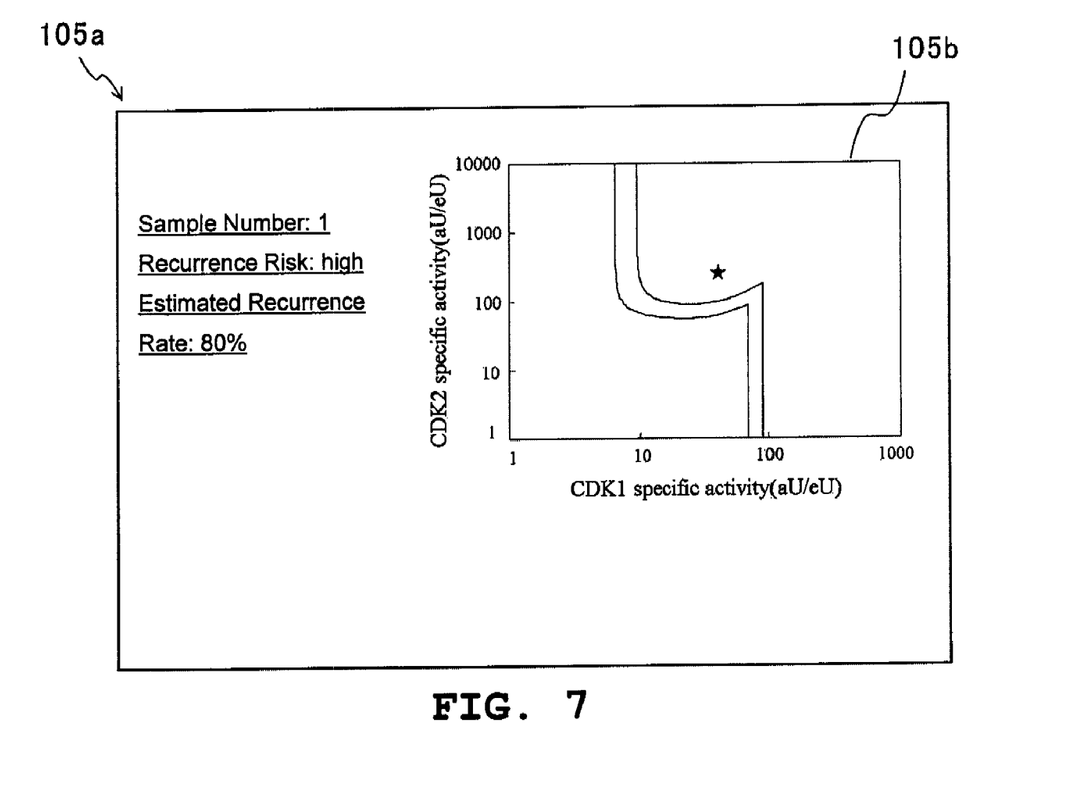
FIG. 7 is an example of a judgment result on a display of the judgment device in this embodiment.

FIG. 7 is a graph showing an example of a display screen of judgment result. As shown in FIG. 7, the judgment result display screen 105a on the display unit 105 displays the sample number of a sample which was judged, recurrence risk judgment result, estimated recurrence rate, and the recurrence risk judgment graph 105b. The estimated recurrence rate is a numerical value displayed based on the recurrence risk judgment result, and for example, 80%, 40% and 10% are displayed when the recurrence risk is "high", "intermediate" and "low", respectively.

The recurrence risk judgment graph 105b is a two-dimensional graph prepared in step S105, and the CDK1 specific activity and CDK2 specific activity of the sample whose recurrence risk has been judged are plotted and displayed (shown by the mark of a star in the graph). By showing the recurrence risk judgment graph together with the recurrence risk judgment result based on the recurrence risk score RRS and the CDK parameter, the degree of recurrence risk in the cancer patient to be examined can be visually known.

The recurrence risk judgment graph in this embodiment has been described by reference to the graph on which the sample whose recurrence was judged, but is not limited to such constitution, and may be constituted as a graph on which a plurality of samples including samples of cancer patients recognized to have cancer recurrence and samples of cancer patients not recognized to have cancer recurrence are plotted. Given such constitution, the risk of cancer recurrence can be statistically known.

This embodiment is constituted by preparing and displaying the recurrence risk judgment graph together with the judgment result of the recurrence risk based on the recurrence risk score RRS, but is not limited to such constitution, and may be constituted so as to display the judgment result of recurrence risk only. In this case, it is not necessary to calculate the CDK parameters in order to prepare the recurrence risk judgment graph, so in this case, the constitution of calculating the CDK parameters may not be arranged.

The judgment device 1 in this embodiment is constituted so as to judge the recurrence risk by calculating the recurrence risk score RRS, but may not be constituted by calculating the recurrence risk score RRS. For example, the judgment device 1 may be constituted such that the CDK parameters are calculated in step S102 in FIG. 6, then a recurrence risk judgment graph having the sample plotted according to the CDK parameters is prepared, and the recurrence risk judgment graph having the sample plotted thereon is displayed. By this constitution, the device for supporting diagnosis, which can realize the method of supporting diagnosis of a risk of cancer recurrence as shown in [1], can be provided. Such device for supporting diagnosis may be constituted so as to judge the recurrence risk based on the position of a sample plotted on the recurrence risk judgment graph, and such change in design also falls under the scope of the invention.

EXAMPLE 1

The judgment method according to this embodiment was used to judge the recurrence risk of cancer patients.

The expression levels and activity values of CDK1 and CDK2 of malignant tumor collected from cancer patients satisfying the following conditions were measured by the method described in the embodiment.
Conditions:
Lymph node metastasis: negative
Endocrine therapy: conducted
Chemotherapy: not conducted
Hormone receptor: positive The obtained expression levels and activity values of CDK1 and CDK2 were used to calculate the recurrence risk score RRS based on the following formulas (12) to (14), and the CDK1 specific activity was calculated based on the following formula (15).

$$RS1; F(x)=0.15/(1+\mathrm{Exp}(-(x-1.6)\times 7)) \quad (12)$$

$$RS2; G(y)=0.25/(1+\mathrm{Exp}(-(y-1.0)\times 6)) \quad (13)$$

$$RRS=3000\times F(x)\times G(y) \quad (14)$$

$x$=CDK1 activity value/CDK1 expression level $y$=(CDK2 activity value×CDK1 expression level)/ (CDK2 expression level×CDK1 activity value)

$$\text{CDK1 specific activity}=\text{CDK1 activity value/CDK1 expression level} \quad (15)$$

Then, the recurrence risk score RRS and CDK1 specific activity obtained from each case were compared with the following conditions to classify the cancer patients into 3 patient groups, i.e. a group of high recurrence risk (High group), a group of low recurrence risk (Low group), and a group of intermediate recurrence risk (Int. group).
Conditions
High group: RRS≧1.47, or
  CDK1 specific activity ≧90 (maU/eU)
Low group: RRS<0.45, and
  CDK1 specific activity <70 (maU/eU)
Int. group: 0.45≦RRS<1.47, and
  70≦CDK1 specific activity <90 (maU/eU)

In each patient group, the number of patients who underwent recurrence within 5 years and the accumulative recurrence rate in each patient group within 5 years were calculated. The results are shown in Table 1.

TABLE 1

| Group | Number of patients | Number of patients with recurrence | Accumulative recurrence rate within 5 years |
|---|---|---|---|
| High | 71 | 9 | 14.1% |
| Low | 83 | 1 | 1.2% |
| Int. | 38 | 3 | 11.7% |

As shown in Table 2, the result of classification of cancer patients by the judgment method in this embodiment revealed that the number of patients corresponding to High group was 71, the number of patients corresponding to Low group was 83, and the number of patients corresponding to Int. group was 38, and the numbers of patients who underwent recurrence within 5 years in the groups were 9, 1, and 3, respectively. The accumulative recurrence rate in each patient group within 5 years was 14.1% in High group, 1.2% in Low group, and 11.7% in the Int. group. It can be seen that the survival of the patients in Low group without recurrence within 5 years is significantly higher than that of the patients in High group. Because the accumulative recurrence rate within 5 years in the parent population is 8.2%, the judgment method in this embodiment can suitably judge the recurrence risk as compared with the parent population. From this result, it was proven that the risk of cancer recurrence in the cancer patients can be accurately judged according to the judgment method in this embodiment.

EXAMPLE 2

The cancer patients in Example 1 were classified with the recurrence risk judgment graph in this embodiment.

First, the expression levels and activity values of CDK1 and CDK2 in the cancer patients were used to calculate the CDK1 specific activity and CDK2 specific activity of each cancer patient, based on the following formulas (16) and (17):

CDK1 specific activity=CDK1 activity value/CDK1 expression level    (16)

CDK2 specific activity=CDK2 activity value/CDK2 expression level    (17)

Figure 8:
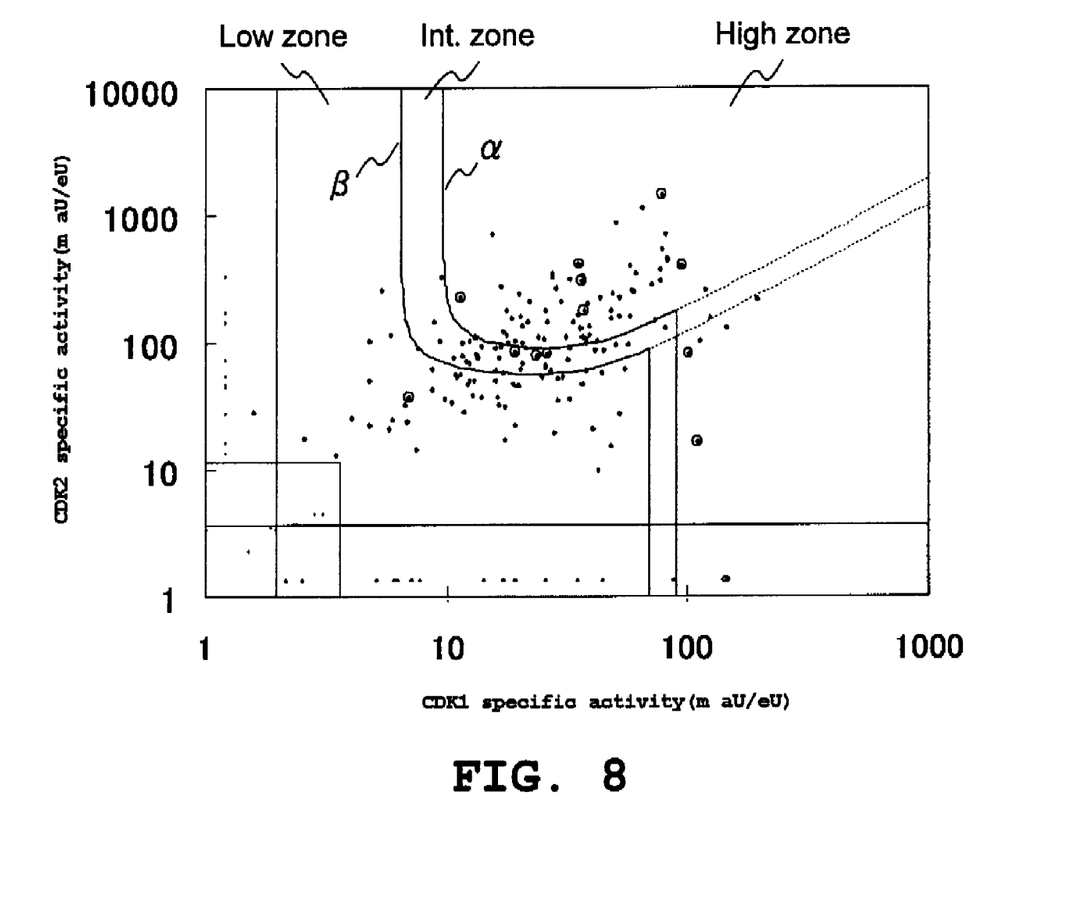
FIG. 8 is a two-dimensional graph on which cancer patients in this example are plotted on CDK1 specific activity (x-axis) and CDK2 specific activity (y-axis).

Based on the resulting CDK1 specific activity and CDK2 specific activity, the cancer patients were then plotted on a recurrence risk judgment graph composed of two parameters, i.e. CDK1 specific activity and CDK2 specific activity, as shown in FIG. 8.

FIG. 8 is a two-dimensional graph wherein the cancer patients in this example are plotted on the basis of CDK1 specific activity (x-axis) and CDK2 specific activity (y-axis), wherein the distribution zone is divided by the cutoff lines α and β into a group of high recurrence risk (High group), a group of low recurrence risk (Low group), and a group of intermediate recurrence risk (Int. group).

In FIG. 8, the cutoff line α is a line wherein a curve drawn by connecting points at which the recurrence risk score RRS value determined from the CDK1 specific activity and CDK2 specific activity is 1.47 is connected to a line drawn by connecting points at which the CDK1 specific activity is 90 (maU/eU). The cutoff line β is a line wherein a curve drawn by connecting points at which the recurrence risk score RRS value determined from the CDK1 specific activity and CDK2 specific activity is 0.45 is connected to a line drawn by connecting points at which the CDK1 specific activity is 70 (maU/eU).

In this figure, the cases where cancer recurrence within 5 years after extirpation of malignant tumor has been undergone are shown by circling.

As a result of classification of the patient groups with the recurrence risk judgment graph, the same classification results as in Table 2 were obtained. From this result, the risk of cancer recurrence in the cancer patients can be suitably judged by using the recurrence risk judgment graph in this embodiment.

From the foregoing, it was suggested that the recurrence risk judgment graph in this embodiment can be displayed in diagnosis support to provide information for supporting highly reliable diagnosis of recurrence risk.

What is claimed is:

1. A method supporting a diagnosis of a risk of cancer recurrence, comprising:
measuring in a malignant tumor sample collected from a patient an expression level of a first cyclin dependent kinase (CDK), an activity value of the first CDK, an expression level of a second CDK and an activity value of the second CDK from a malignant tumor collected from a cancer patient to be examined;
calculating a recurrence risk score by a first formula comprising recurrence risk score=$F(X) \times G(Y)$, wherein X represents a first CDK specific activity which is a ratio of the activity value of the first CDK to the expression level of the first CDK,
wherein Y represents a specific activity ratio which is a ratio of a second CDK specific activity to the first CDK specific activity,
wherein the second CDK specific activity is a ratio of the expression level of the second CDK to the activity value of the second CDK,
wherein F(X) is a function of a correlation of X with a cancer recurrence rate, and
wherein G(Y) is a function of a correlation of Y with the cancer recurrence rate.

2. The method of claim 1, further comprising judging a risk of cancer recurrence.

3. The method of claim 2, wherein the judging of the risk of cancer recurrence is conducted by comparing the recurrence risk score with a predetermined threshold value.

4. The method of claim 2, further comprising calculating a first CDK specific activity from the expression level of the first CDK and the activity value of the first CDK acquired from the malignant tumor.

5. The method of claim 4, wherein the judging of the risk of cancer recurrence comprises:
comparing the recurrence risk score with a first threshold value; and
comparing the first CDK specific activity with a second threshold value.

6. The method of claim 5, wherein in the judging of the risk of cancer recurrence, the risk of cancer recurrence is judged to be high when the recurrence risk score is equal to or higher than the first threshold value, or the first CDK specific activity is equal to or higher than the second threshold value.

7. The method of claim 1, wherein:
F(X) is represented by a second formula comprising $F(X)=a/(1+\text{Exp}(-(X-b) \times c))$, and G(Y) is represented by a third formula comprising $G(Y)=d/(1+\text{Exp}(-(Y-e) \times f))$, wherein a to f represent a constant.

8. A method supporting a diagnosis of a risk of cancer recurrence, comprising:
measuring in a malignant tumor sample collected from a patient an expression level of a first cyclin dependent kinase (CDK), an activity value of the first CDK, an expression level of a second CDK and an activity value of the second CDK from a malignant tumor collected from a cancer patient to be examined;
calculating a first CDK specific activity which is calculated by using a ratio of the expression level and the activity value of the first CDK, and a second CDK specific activity which is calculated by using a ratio of the expression level and the activity value of the second CDK; and
displaying a recurrence risk judgment graph which comprises at least two parameters of a first CDK specific activity and a second CDK specific activity, and is divided into zones different in a recurrence risk score calculated by a fourth formula comprising recurrence risk score=$F(X) \times G(Y)$, wherein the cancer patients to be examined are plotted based on the first CDK specific activity and the second CDK specific activity on the judgment graph, wherein X represents a first CDK specific activity;

wherein Y represents a specific activity ratio which is a ratio of the first CDK specific activity to the second CDK specific activity, wherein F(X) is a function of a correlation of X with a cancer recurrence rate, and wherein G(Y) is a function of a correlation of Y with the cancer recurrence rate.

9. The method of claim 8, wherein:

the judgment graph is divided by a first standard line that divides the judgment graph into zones different in recurrence risk score and by a second standard line that shows a predetermined first CDK specific activity.

10. The method of claim 8, further comprising:

judging a risk of cancer recurrence by using the recurrence risk judgment graph and a plotted cancer patient to be examined; and displaying a judgment result of the risk of cancer recurrence together with the recurrence risk judgment graph.

11. A device supporting a diagnosis of a risk of cancer recurrence, comprising:

measurement section measuring a malignant tumor collected from a cancer patient to be examined to acquire an expression level of a first cyclin dependent kinase (CDK), an activity value of the first CDK, an expression level of a second CDK and an activity value of the second CDK; and a controller including a memory under control of a processor, the memory storing instructions enabling the processor to carry out operations which comprise calculating a recurrence risk score by a fifth formula comprising recurrence risk score=$F(X) \times G(Y)$, wherein X represents a first CDK specific activity which a ratio of the activity value of the first CDK to the expression level of the first CDK;

wherein Y represents a specific activity ratio which is a ratio of a second CDK specific activity to the first CDK specific activity, wherein the second CDK specific activity is a ratio of the expression level of the second CDK to the activity value of the second CDK, wherein F(X) is a function of a correlation of X with a cancer recurrence rate, and wherein G(Y) is a function of a correlation of Y with the cancer recurrence rate.

12. The device of claim 11, wherein:

the operations further comprise judging a risk of cancer recurrence.

13. The device of claim 12, wherein the judging of the risk of cancer recurrence is conducted by comparing the recurrence risk score with a predetermined threshold value.

14. The device of claim 12, wherein:

the operations further comprise calculating a first CDK specific activity from the expression level of the first CDK and the activity value of the first CDK acquired from the malignant tumor.

15. The device of claim 14, wherein the judging of the risk of cancer recurrence comprises:

comparing the recurrence risk score with a first threshold value; and comparing the first CDK specific activity with a second threshold value.

16. The device of claim 15, wherein in the judging of the risk of cancer recurrence, the risk of cancer recurrence is judged to be high when the recurrence risk score is equal to or higher than the first threshold value, or the first CDK specific activity is equal to or higher than the second threshold value.

17. The device of claim 11, wherein:

F(X) is represented by a sixth formula comprising $F(X)=a/(1+\mathrm{Exp}(-(X-b) \times c))$, and G(Y) is represented by a seventh formula comprising $G(Y)=d/(1+\mathrm{Exp}(-(Y-e) \times f))$, wherein a to f represent a constant.

18. A device supporting a diagnosis of a risk of cancer recurrence, comprising:

measurement section measuring a malignant tumor collected from a cancer patient to be examined to acquire an expression level of a first cyclin dependent kinase (CDK), an activity value of the first CDK, an expression level of a second CDK and an activity value of the second CDK; and a controller system including a display and a memory under control of a processor, the memory storing instructions enabling the processor to carry out operations, comprising:

calculating a first CDK specific activity which is calculated by using a ratio of the expression level and the activity value of the first CDK acquired by the measurement section, and a second CDK specific activity which is calculated by using a ratio of the expression level and the activity value of the second CDK acquired by the measurement section; and displaying a recurrence risk judgment graph which comprises at least two parameters of a first CDK specific activity and a second CDK specific activity, and is divided into zones different in a recurrence risk score calculated by an eighth formula comprising recurrence risk score=$F(X) \times G(Y)$, wherein the cancer patients to be examined are plotted based on the first CDK specific activity and the second CDK specific activity on the judgment graph, wherein X represents a first CDK specific activity;

wherein Y represents a specific activity ratio which is a ratio of the first CDK specific activity to the second CDK specific activity, wherein F(X) is a function of a correlation of X with a cancer recurrence rate, and wherein G(Y) is a function of a correlation of Y with the cancer recurrence rate.

19. The device of claim 18, wherein the judgment graph is divided by a first standard line that divides the judgment graph into zones different in recurrence risk score and by a second standard line that shows a predetermined first CDK specific activity.

20. The device of claim 18, wherein the operations further comprise:

judging a risk of cancer recurrence by using the recurrence risk judgment graph and a plotted cancer patient to be examined; and displaying a judgment result of the risk of cancer recurrence together with the recurrence risk judgment graph.

* * * * *